US006869397B2

(12) United States Patent
Black et al.

(10) Patent No.: US 6,869,397 B2
(45) Date of Patent: Mar. 22, 2005

(54) NON-TETHERED MACRO-TO-MICRO ENDOSCOPE

(75) Inventors: Michael D. Black, Palo Alto, CA (US); Purna Prasad, Santa Clara, CA (US); Terry E. Robinson, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 190 days.

(21) Appl. No.: 10/159,976

(22) Filed: May 31, 2002

(65) Prior Publication Data

US 2003/0009086 A1 Jan. 9, 2003

Related U.S. Application Data

(60) Provisional application No. 60/295,122, filed on Jun. 1, 2001.

(51) Int. Cl.$^7$ ............................ A61B 1/04; A61B 1/06
(52) U.S. Cl. ..................... 600/168; 600/112; 600/181; 600/178
(58) Field of Search ........................ 600/112, 168, 600/181, 109, 118, 172, 173, 177, 178, 160; 348/73, 72, 74, 75

(56) References Cited

U.S. PATENT DOCUMENTS

| | | | |
|---|---|---|---|
| 4,253,447 A | | 3/1981 | Moore et al. |
| 4,736,734 A | * | 4/1988 | Matsuura et al. ........... 600/110 |
| 4,860,094 A | | 8/1989 | Hibino et al. |

(List continued on next page.)

FOREIGN PATENT DOCUMENTS

| JP | 1-197716 | * 8/1989 |
|---|---|---|

OTHER PUBLICATIONS

Helm, et al., "Accuracy of Registration Methods in Frameless Stereotaxis," Computer Aided Surgery, 3:51–56, 1998.
Vorbeck, et al., "Experiences in Intraoperative Computer–Aided Navigation in ENT Sinus Surgery with the Aesculap Navigation System," Computer Aided Surgery, 3:306–311, 1998.
Kim, et al., "Virtual Tape Measure for the Operating Microscope: System Specifications and Performance Evaluation," Computer Aided Surgery, 5:148–155, 2000.
Greenberg, et al., "Novel Method for Stereo Imaging in Light Microscopy at High Magnifications," Neuroimage, 1:121–128, 1993.
Nishioka, et al. "Initial Experience with a Real–Time Video Processor for Enhancing Endoscopic Image Contrast," Gastrointestinal Endoscopy, vol. 48, No. 1, 62–66, 1998.
Davies, et al., New Avenues in 3–D Computerised (Stereopathological) Imaging of Breast Cancer (Review), Anticancer Research, 16:3971–3982, 1996.

(List continued on next page.)

*Primary Examiner*—John P. Leubecker
(74) *Attorney, Agent, or Firm*—Lumen; Intellectual Property Services, Inc.

(57) ABSTRACT

An endoscope to perform non-tethered macroscopy and microscopy at the same time is provided. An electromagnetic source is used to deliver electromagnetic energy through a first optical pathway to a tissue inside a body. An image detector is used to detect the reflected electromagnetic energy from the tissue through a second optical pathway as real-time images. A macro-to-micro lens set is used to change the magnification of the reflected electromagnetic energy before it reaches the image detector with two or more different magnification levels. A filter set is used to filter the reflected electromagnetic energy before it reaches the image detector. Furthermore, the endoscope includes a flexible shaft. The distal end of the shaft includes a spread and spot means to spread and spot the electromagnetic energy at the tissue. A processing means is also included for processing the detected images.

48 Claims, 6 Drawing Sheets

U.S. PATENT DOCUMENTS

| | | | |
|---|---|---|---|
| 4,901,142 A | | 2/1990 | Ikuno et al. |
| 4,947,245 A | | 8/1990 | Ogawa et al. |
| 5,278,642 A | * | 1/1994 | Danna et al. ............... 348/70 |
| 5,430,475 A | | 7/1995 | Goto et al. |
| 5,547,455 A | | 8/1996 | McKenna et al. |
| 5,653,677 A | | 8/1997 | Okada et al. |
| 5,682,199 A | | 10/1997 | Lankford |
| 5,737,121 A | | 4/1998 | Dixon |
| 5,836,869 A | * | 11/1998 | Kudo et al. ............... 600/173 |
| 5,940,126 A | | 8/1999 | Kimura |
| 5,971,919 A | * | 10/1999 | Davis ............... 600/180 |
| 6,028,622 A | | 2/2000 | Suzuki |
| 6,059,721 A | | 5/2000 | Rudischhauser et al. |
| 6,120,435 A | | 9/2000 | Eino |
| 6,141,037 A | | 10/2000 | Upton et al. |
| 6,181,368 B1 | | 1/2001 | Takahashi et al. |
| 6,184,922 B1 | | 2/2001 | Saito et al. |
| 6,184,923 B1 | | 2/2001 | Miyazaki |
| 6,195,119 B1 | | 2/2001 | Dianna et al. |
| 6,224,542 B1 | | 5/2001 | Chang et al. |
| 6,450,949 B1 | * | 9/2002 | Farkas et al. ............... 600/168 |
| 6,530,882 B1 | * | 3/2003 | Farkas et al. ............... 600/168 |
| 6,554,765 B1 | * | 4/2003 | Yarush et al. ............... 600/132 |
| 6,641,531 B2 | * | 11/2003 | Kehr ............... 600/172 |
| 2002/0013513 A1 | | 1/2002 | Bala |
| 2002/0026093 A1 | | 2/2002 | Ooyatsu |
| 2002/0033882 A1 | | 3/2002 | Wada et al. |

OTHER PUBLICATIONS

Furuta, et al., "A New in Vivo Staining Method, Cresyl Violet Staining, for Fiberoptic Magnified Observation of Carcinoma of the Gastric Mucosa," Gastroenterologia Japonica, vol. 20, No. 2, 120–124, 1985.

Matsumoto, et al., "Application of Magnifying Chromoscopy for the Assessment of Severity in Patients with Mild to Moderate Ulcerative Colitis," Gastrointestinal Endoscopy, vol. 46, No. 5, 400–405, 1997.

Cales, et al., "Gastric Mucosal Surface in Cirrhosis Evaluated by Magnifying Endoscopy and Scanning Electric Microscopy," Endoscopy, 32(8):614–623, 2000.

Shpakov, et al., "Bronchoscopic Methods in Complex Diagnosis and Treatment of Burned Patients with Inhalation Injuries," Vestn Khir Im II Grek, 158(3):34–37, 1999.

* cited by examiner

NON-TETHERED MACRO-TO-MICRO ENDOSCOPE

CROSS-REFERENCE TO RELATED APPLICATIONS

This application is cross-referenced to and claims priority from U S. Provisional Application 60/295,122 filed on Jun. 1, 2001, which is hereby incorporated by reference.

FIELD OF THE INVENTION

The present invention relates generally to medical systems. More particularly, the present invention relates to a non-tethered endoscope to acquire macroscopic and microscopic video and still images during endoscopic and surgical procedures.

BACKGROUND

Endoscopy is a medical field which allows the acquisition of images of internal features of a human body, without the need for invasive surgery. A basic tool of endoscopy is an endoscopic camera system, which includes a scope or shaft that is inserted into the body of a patient. Some endoscopic procedures involve the use of a flexible shaft such as, for instance, in the field of gastroenterology. Other procedures involve the use of a rigid shaft such as, for instance, in the field of arthroscopy, thorascopy or laparoscopy. The shaft is normally connected to a camera head that includes electronics for acquiring the image data through the shaft.

The connected shaft and camera head may be held and manipulated during endoscopic surgery by a user (e.g. a surgeon) or by a holding tool, such as a robotic positioning system. The shaft has optical properties which allows it to introduce light into the body of the patient and to transmit light from the body cavity to the camera head. A high intensity light source may be coupled to the shaft by a fiber optic cable to introduce light into the body. The camera head is coupled through a flexible transmission line to a camera control unit, which is often mounted on a mobile cart. The control unit processes video data provided by the camera head to generate images, which are displayed on a video monitor. The control unit may also be coupled to various peripheral devices, such as a printer and a video cassette recorder.

During endoscopic surgery, the surgeon sometimes requires a more close-up view of a feature inside the body. One way of accomplishing this is for the person or machine holding the scope to physically move the scope closer to the feature of interest. This approach has several disadvantages. For example, physically moving the scope consumes valuable time during the surgery while the scope is repositioned. The repositioning process may involve several trial and error steps as the surgeon makes corrections in response to verbal feedback from the surgeon. It may be difficult for a human holder to maintain the scope in precisely the desired position, particularly when fatigue sets in. Furthermore, moving the scope closer to the object of interest might interfere with the surgeon's ability to operate and could potentially heat the object of interest causing damage or trauma to the object of interest.

Some endoscopic camera systems provide the capability to zoom in on an object without having to move the scope closer to the object. However, with such zooming capability, adjusting the configuration of the optics within the scope and/or its connections to the camera head is required. This may be done manually or electronically by pressing a button or other appropriate control. However, these systems require time to adjust and are subject to a certain amount of trial-and-error in zooming. Furthermore, zooming might cause the surgeon to undesirably loose view of the general field of surgery within the body. Reacquiring the more general view requires reverting the zoom lens to a lower magnification setting. Accordingly, it is desirable to have an endoscopic system that overcomes these and other disadvantages of the current endoscopic systems, yet provides the required flexibility and versatility to meet today's endoscopic demands and needs to perform clinical macroscopy and microscopy. For example, other disadvantages of current endoscopic systems could be characterized as: (a) a requirement of a translucent medium (e.g. gas or liquid) in order to visualize the object of interest, (b) limited visibility of the object of interest due to a small range of magnification mostly in the range of 10× to 20×, or (c) imprecise and awkward manipulation due to various cables and connectors in case of a tethered endoscope.

SUMMARY OF THE INVENTION

The present invention provides an endoscope to perform non-tethered macro-to-micro endoscopy and generate real-time macroscopic and microscopic images with the same endoscope. The endoscope of the present invention could be used as a catheter-based endoscope, a percutaneous endoscope, a transvascular endoscope or a trans-lymphatic endoscope. Furthermore, the endoscope of the present invention is not dependent on a translucent medium and can therefore be used with or without a translucent medium. The endoscope of the present invention operates completely non-tethered which is enabled through a wireless communications between the endoscope, control means and processing means.

The endoscope of the present invention includes an electromagnetic source to deliver electromagnetic energy through a first pathway to a tissue inside a body. The electromagnetic source is a light source or a modulated energy source in an electromagnetic spectrum. The endoscope further includes an image detector to detect the reflected electromagnetic energy from the tissue through a second pathway. The first and second pathway could be an optical pathway for optical wavelengths or a pathway for other electromagnetic wavelengths. The reflected electromagnetic energy is detected as real-time images. Examples of image detectors are, for instance, one or more CCD cameras, one or more ultrasound transducers, one or more infrared transducers, or one or more microwave transducers. The endoscope further includes a macro-to-micro lens set to change the magnification of the reflected electromagnetic energy before it reaches the image detector. The macro-to-micro lens set enables a user to perform macroscopy and microscopy with the same endoscope. An example of macro-to-micro lens set is a lens set with 1× magnification for macroscopy (i.e. 1:1) and 10×, 100× and 200× magnification for microscopy. The reflected electromagnetic energy passes through a lens set with two or more of the lenses 1×, 10×, 100× or 200× before reaching the image detector. The macro-to-micro lens set is not limited to these types of magnifications, and in general the magnification of the lenses in the macro-to-micro lens set could range from 1× to 200×. The key idea of the macro-to-micro lens set is to provide two or more magnifications at the same time. The endoscope of the present invention further includes a filter set to filter the reflected electromagnetic energy before it reaches the image detector. The filter set includes at least one type of filter and could change the luminescence or the chrominance of the electromagnetic energy. The endoscope of the present invention can be a single device including the source, magnification lens set, filter set and image detector or can be a device build up from modules based on the source, magnification lens set, filter set and image detector. Furthermore, the endoscope of the present invention includes a shaft (flexible or rigid) that can also be an integral part of the endoscope of a modular component. The shaft could also include an addition modular component that includes a distal shaft module. The distal end of the shaft includes a spread and spot means to spread and spot the electromagnetic energy at the tissue. The endoscope could optionally include a plurality of channels that extend through the endoscope which allow the surgeon to perform various kinds of interventions or surgical procedures. The endoscope includes control means to control the electromagnetic source, the macro-to-micro lens set, the filter set, flexible shaft, spread and spot means, and optionally a distal end of the shaft. The control means could be accomplished by a user-hand control panel or a voice command control system.

The present invention further includes a processing means for processing the detected images. The processing means could include means for magnification, staining or electronic filtering of the detected images as well as real-time processing of the detected images. Processing means further includes a means for image localization which could be enabled by a computerized image navigation system to navigate the endoscope to a marked location in the image. The present invention also includes means for displaying the images.

In view of that which is stated above, it is the objective of the present invention to provide an endoscope that is completely non-tethered and allows a user to perform microscopy and macroscopy with the same device.

It is still another objective of the present invention to provide an endoscopic system based on modular components that are interchangeable.

It is still another objective of the present invention to provide an endoscopy that is able to operate in the electromagnetic spectrum.

It is still another objective of the present invention to provide an endoscope with a macro-to-micro magnification lens set with two or more different magnifications.

It is yet another objective of the present invention to provide an endoscope with spread and spot capabilities to deliver the electromagnetic energy at the tissue site.

It is yet another objective of the present invention to provide an ergonomic user-hand control panel.

It is yet another objective of the present invention to provide a voice command control system to operate the endoscope.

The advantage of the present invention over previous devices and methods is that the endoscope of the present marker device allows a user to perform macroscopy and microscopy with the same endoscope. Yet another advantage is that endoscope of the present invention is completely non-tethered which increases the mobility of using the endoscope. Yet another advantage is that the present invention is not restricted to environments with a translucent medium and could be used with or without a translucent medium.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides an endoscope to perform non-tethered macro-to-micro endoscopy. The endoscope of the present invention can be used for numerous applications for various kinds of endoscopic services, such as, but not limited to, flexible fiberoptic bronchoscopy, colonscopy, and other endoscopy, as well as a surgical, interventional, and pathological interface for surgical specialties, cardiology, gastroenterology, pulmonology, and pathology. In general, as a person of average skill in the art would readily appreciate, the endoscope of the present invention could be used in microscopy and macroscopy applications related to endoscopy, surgery, surveillance and intervention. Furthermore, the present invention could also be used for catheter-based endoscopy, percutaneous endoscopy, trans-vascular endoscopy or trans-lymphatic endoscopy. It is important to realize that the endoscope of the present invention does not require a translucent medium, such as a gas or liquid, and can therefore be characterized as an endoscope that can be used with or without a translucent medium.

Figure 1:
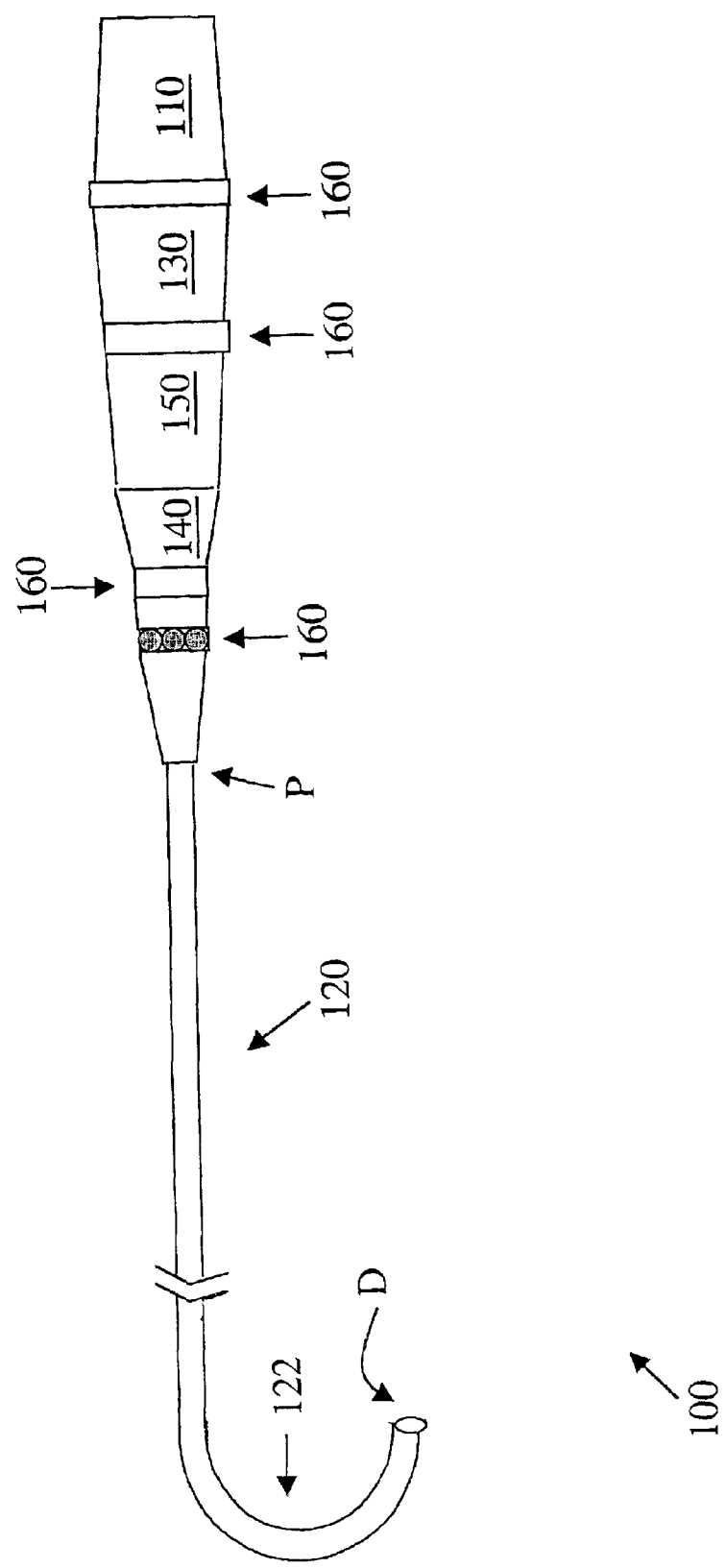
FIG. 1 shows an exemplary embodiment of an endoscope according to the present invention.

FIG. 1 shows an embodiment of endoscope 100 of the present invention. Endoscope 100 is a completely non-tethered endoscope and includes various interchangeable modules that can easily be replaced by other modules meeting the requirement of a particular intervention. Examples of various modules as described below are a module for the delivery of electromagnetic energy, a module for magnifying the reflected electromagnetic energy, a module for filtering the reflected electromagnetic energy, a module for detection the reflected electromagnetic energy, as well as a modular system for the entire shaft or a part of the shaft (e.g. the distal part) of the endoscope. The modularity also allows endoscope 100 to maintain relatively small and lightweight as well as flexible and versatile in use compared to current endoscopes. Endoscope 100 includes an electromagnetic source 110 to deliver electromagnetic energy through a shaft 120 of endoscope 100 to a tissue inside a body. The electromagnetic source 110 could be any type of light source or modulated energy source in the electromagnetic spectrum within the wavelength region extending from the vacuum ultraviolet at 40 nm to the far-infrared at 1 mm.

Examples of electromagnetic source 110 are, for instance, but not limited to, Xenon light sources, ultrasound transmitters, infrared transmitters or microwave transmitters. The range of electromagnetic source 110 enables a user to perform diagnostics as well as treatment of the tissue of interest. The type of module of electromagnetic source 110 that can be added to endoscope 100 is dependent on the type of endoscopy a user expects to perform as well as the range of wavelengths that are needed for diagnostic or treatment purposes. Dependent on the size of the various kinds of electromagnetic sources, electromagnetic source 110 could include different kinds of electromagnetic sources in a single module that can be selected during an endoscopic procedure. The electromagnetic energy generated by electromagnetic source 110 travels through an pathway in shaft 120, preferably through a fiber optical cable or a bundle of optical fibers in case of optical wavelengths or a pathway suitable for other electromagnetic wavelengths as a person of average skill would readily appreciate. Electromagnetic source 110 could be attached to endoscope 100 through an angled attachment with, for instance, a confocal lens to distribute the electromagnetic energy intensity uniformly to a bundle of optical fibers. Another optical pathway traveling through shaft 120 also preferably includes a fiber optic bundle and is used to transmit the reflected electromagnetic energy back from the distal part D to the proximal part P of the endoscope. The pathway is a suitable pathway for other electromagnetic wavelengths as a person of average skill would readily appreciate. The reflected electromagnetic energy will be detected by image detector 130 after passing through a filter set 140 and through a macro-to-micro lens set 150 (the position of magnification lens set and filter set could be interchanged).

Image detector 130 detects reflected electromagnetic energy from the tissue in the body. Image detector 130 could include one or more CCD cameras, one or more ultrasound transducers, one or more infrared transducers, or one or more microwave transducers. An example of image detector 130 of a CCD camera is a 3 CCD architecture; one CCD for red color processing, one for green color processing, and one for blue color processing. Image detector 130 is also modular and dependent on the type of endoscopy that is anticipated to be performed, the user could select the appropriate type of image detector and inserts that module in endoscope 100. The selection of image detector 130 also coincides with the selection of electromagnetic source 110. Dependent on the size of the various kinds of image detectors, image detector 130 could also include different kinds of detectors in a module that can be selected during an endoscopic procedure.

Figure 2:
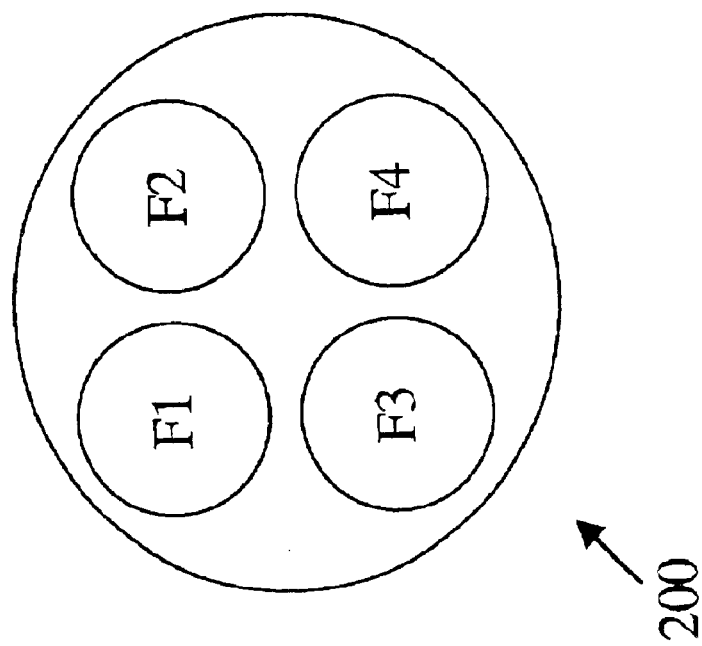
FIG. 2 shows an exemplary embodiment of a filter set according to the present invention.

Filter set 140 filters the reflected electromagnetic energy. Filter set 140 includes filters for changing the luminescence or changing the chrominance of the reflected electromagnetic energy. FIG. 2 shows an exemplary embodiment of a filter set 200 with four different filters F1, F2, F3 and F4. However, filter set 200 could include any variety of filters and any number of filters and is not limited to 4 filters as shown in FIG. 2. In general, red, blue and green filters or a combination of one of these filters could be used. Again, filter set is a modular component of the endoscope of the present invention. Therefore filter set could be replaced with another and different filter set to meet the requirements and objectives of the endoscopic intervention.

Figure 3:
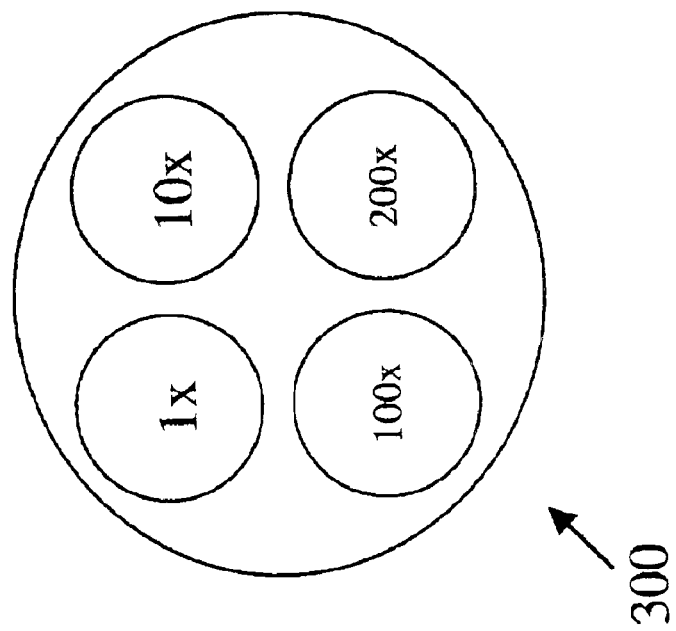
FIG. 3 shows an exemplary embodiment of a macro-to micro lens set according to the present invention.

Macro-to-micro lens set 150 enables a user to perform macroscopy and microscopy. FIG. 3 shows an example of macro-to-micro lens set 300 with 1× for macroscopy (i.e. 1:1) and 10×, 100× and 200× magnification for microscopy. The reflected electromagnetic energy passes through one of the lenses of a lens set which contains two or more of the lenses before reaching image detector 130. These lenses provide magnifications of 1×, 10×, 100× or 200×. Macro-to-micro lens set 300 is not limited to these types of magnifications, and in general the magnification of the lenses in macro-to-micro lens set 300 could range from 1× to 200×. The modularity of endoscope 100 also allows macro-to-micro lens set to be changed as an individual module with another macro-to-micro lens set module. The present invention therefore enables a user to acquire both near and far field motion and still images during endoscopic procedures.

Electromagnetic source 110, image detector 130, filter set 140, macro-to-micro lens set 150, and shaft 120 (or a part of a shaft such as a distal part of shaft 120) could each also include means to change to a particular source in electromagnetic source 110, to a particular detector in image detector 130, to a particular filter in filter set 140 or to a particular lens in macro-to-micro lens set 150, or to a particular orientation of shaft 120, respectively. This could, for instance, be accomplished by rotating each respective module either by hand, by motor controlled concentric rings with ball bearing for 360 degrees motion as indicated by mounting adapter 160 or through a user-hand control panel as is discussed with reference to FIG. 5 below. However, the preferred way of accomplishing a change in one of the modules would be through voice commands, i.e. a hands-off control system. The surgeon could then change or control the endoscope of the present invention through voices commands as it is known in the art of computer science and artificial intelligence as well as in some medical applications.

Shaft 120 could be a rigid or a flexible shaft. Furthermore, shaft 120 could be at a fixed length or could include means for a telescopic movement to change the shaft's length to move into the body or retract from the body. The endoscope of the present invention could also include a distal shaft module that could be placed or replace the distal part of the endoscope. Such a distal shaft module could, for instance, replace a flexible distal shaft into a distal shaft with telescopic means to provide retraction and/or extension of the shaft into the body. A telescopic means could be accomplished by having two or more segment telescopically combined (not shown). In another embodiment of a flexible shaft, the distal part 122 of shaft 120 could also include means to bend or rotate distal part 122 of shaft 120. The shaft also includes means to rotate the entire shaft 120, around its longitudinal axis, wherein the control means is preferably placed at the proximal end of shaft 120. Such a control means could be enabled in a similar fashion as for the other modules as is described above.

In another embodiment, shaft 120 could include a plurality of segments that allow for telescopic and flexible movements of shaft 120. The endoscope of the present invention is, however, not limited to a particular means or mechanism and could therefore include any other means or mechanisms that allow for flexibility and maneuverability of shaft 120, some of which are already known in the art. In case of a telescopic shaft, the telescopic movement of the shaft then also moves the fiberoptic cables using fine motor control devices or means alike.

Figure 4:
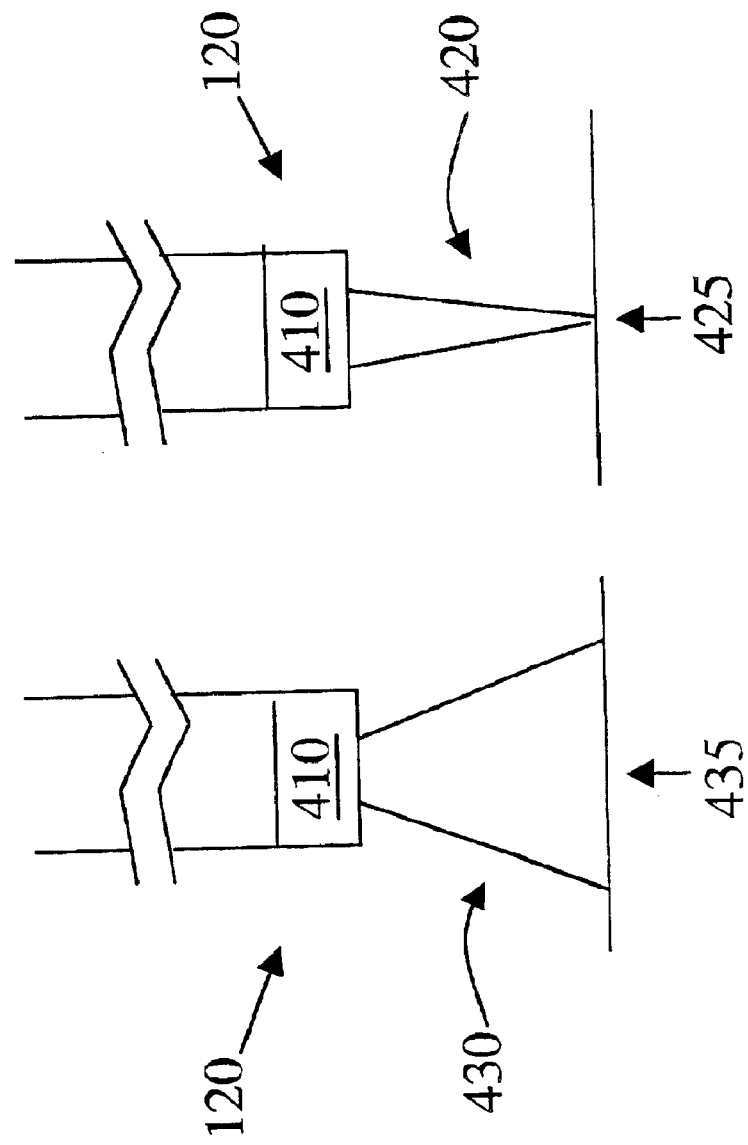
FIG. 4 shows an exemplary embodiment of the spread and spot capability of the endoscope according to the present invention.

FIG. 4 shows the distal end of shaft 120 with a means 410 (e.g. a concentric outer ring) to enable a user to vary the field of view by spot 420 and spread 430 actions of the electromagnetic energy to a area of interest 425 and 435, respectively. Examples of such a lens are, for instance, a focal lens or a Frenel lens.

Both flexible and rigid shaft designs could also include a plurality of channels (not shown) for therapeutic and diagnostic drug delivery, patch clamp data collection, radio nuclei tags, etc. The requirement for the channels is that there is enough room for effective (1) suction (yield of sputum is approximately equal to area of cross section of the channel and negative pressure—vortex suction motion), (2) biopsy, (3) patch clamping, (4) staining/electronic marking, (5) genetic marking, or the like.

Figure 5:
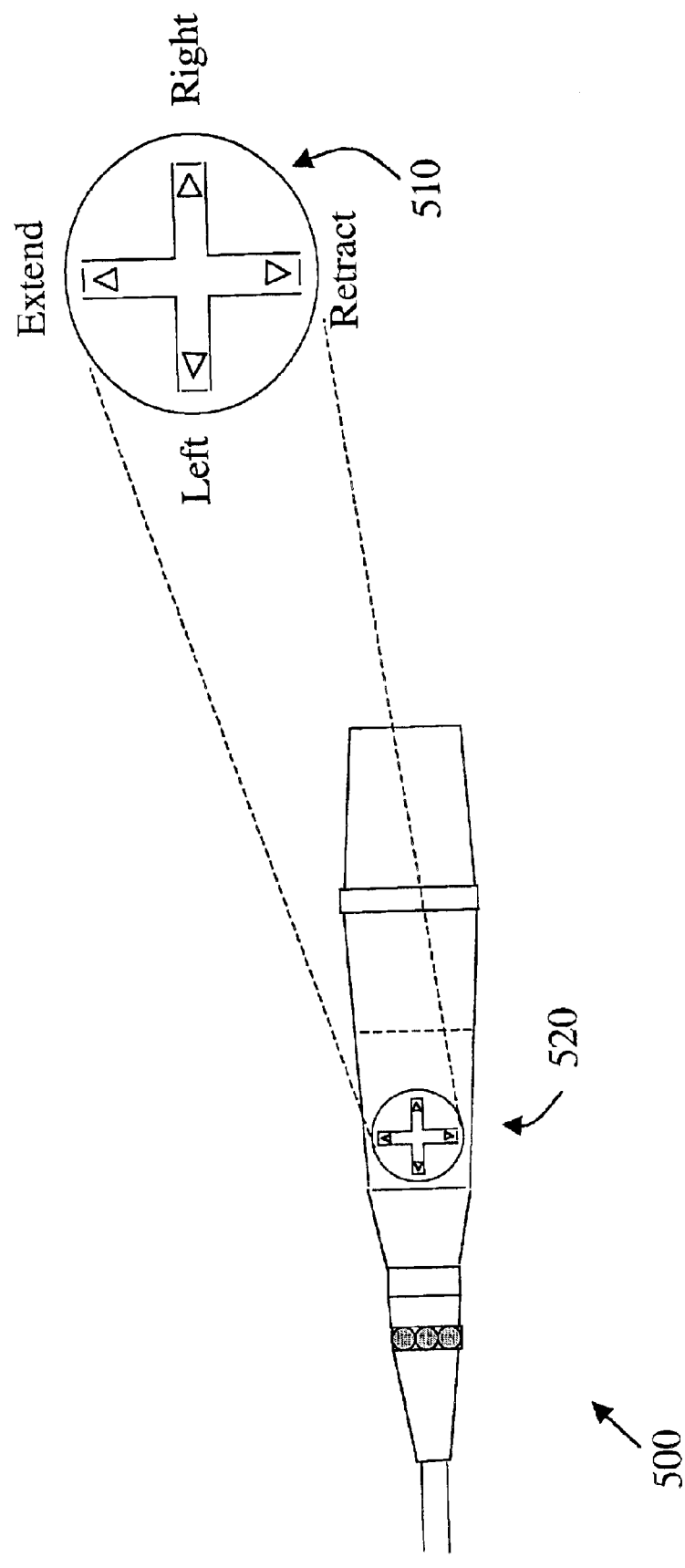
FIG. 5 shows exemplary embodiment of a user-hand control panel according to the present invention.

The endoscope of the present invention further includes a user-hand control panel 510 to control endoscope 500 as shown in FIG. 5. FIG. 5 shows one embodiment of control panel 510 with four click buttons; i.e. one for extension of the shaft of the endoscope (extend), one for retraction of the shaft of the endoscope (retract), one for moving the shaft of the endoscope leftward (left), and one for moving the shaft of the endoscope rightward (right). However, as a person of average skill would readily appreciate, user-hand control panel 510 can include a variety of different control buttons and functions For instance, the control for selecting the type of electromagnetic source, type of filter, type of lens or type of image detector in each of their respective modules could be included. The user-hand control panel 510 could also include buttons with combined actions. A combined action could, for instance, be a rotation of the shaft with an extension of the shaft while flexing the distal end of the shaft. Furthermore, the user-hand control panel 510 could also be programmable through a wireless interface which is described below.

The position of user-hand control panel 510 is preferably in a place so that when a user holds hand-piece 520 of endoscope 500, the tip of the fingers of that user are nicely placed over the user-hand control panel 510 to easily push the desired buttons. This objective is to provide a better endoscope-user interface. Furthermore, user-hand control panel 510 is not limited to click buttons and could include any type of interface or switch to initiate control function to endoscope 500.

Figure 6:
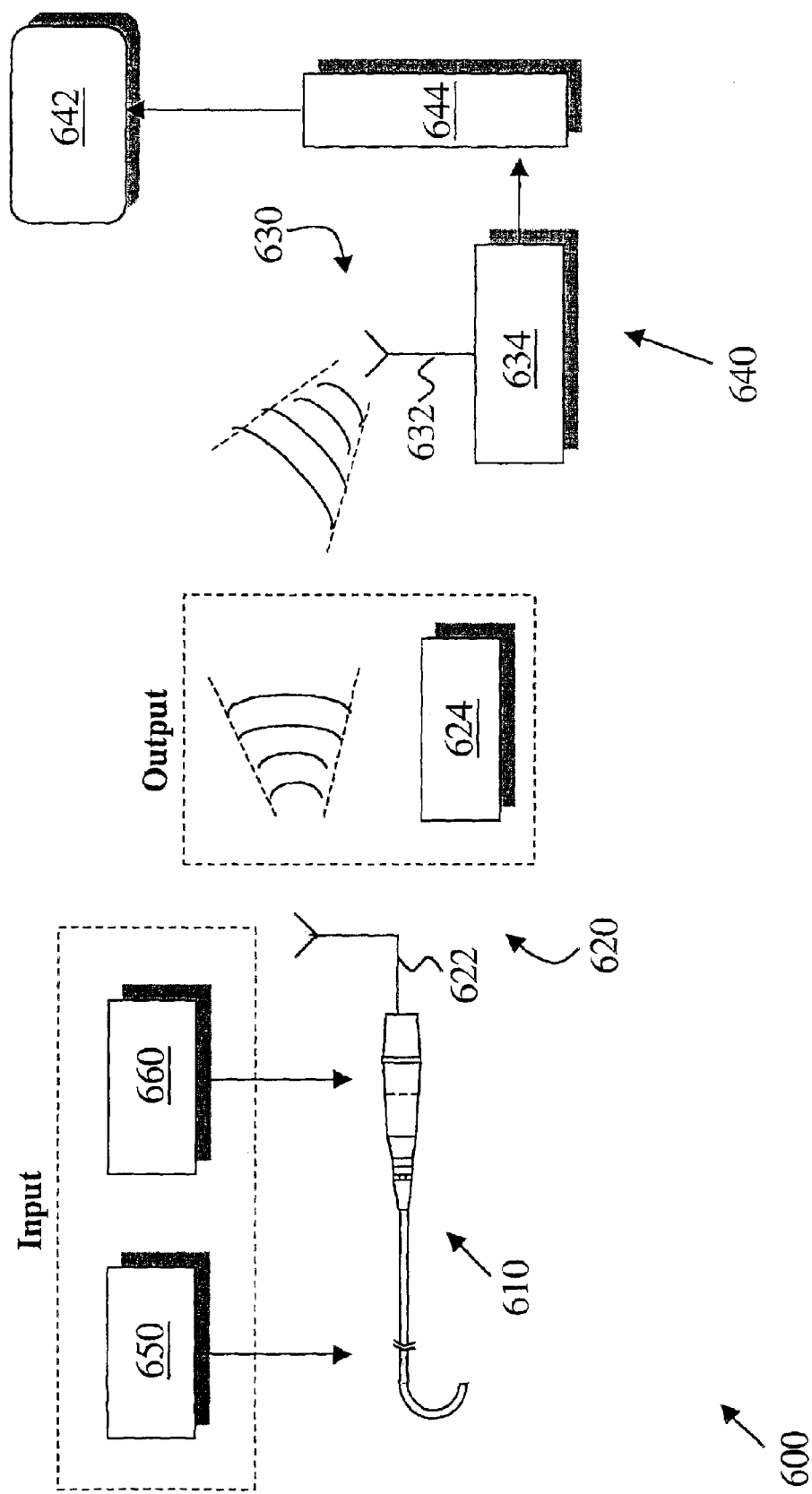
FIG. 6 shows an exemplary embodiment of the real-time and wireless transmission between endoscope and a processing means according to the present invention.

FIG. 6 shows an embodiment 600 of the present invention wherein the endoscope 610 operates as a completely non-tethered endoscope. Endoscope 610 includes a wireless communication system for transmitting 620 (using antenna 622 and transmitter 624) and receiving 630 (using antenna 632 and transmitter 634) audio, video, and data to and from endoscope 610 to a processing means 640. Processing means 640 usually includes a display 642 (such as, for instance, a plasma flat panel display) and a computer 644. Display 642, for instance, display one or more fields of visualization or images, a processing or analyzing display area to display software to process or analyze some of the images, a navigation display to navigate to a (previously) recognized object of interest, other types of images such as CT or MR images, or other type of display screens that would result from the use of the endoscope of the present invention. Processing means could also include a communication network, such as an Internet and Intranet (not shown). Processing means 640 processes the received data (video and audio) from endoscope 610 and processes the data in real-time. Processing means 610 further includes means for image localization to localize a tissue of interest. The marked location allows the processing means 640 to navigate endoscope 610 automatically to and from the marked location. This navigation could be established by computerized image navigation techniques, some of which are known in the art of image processing. It would also be feasible that endoscope 610 could be automatically navigated to a previously marked location in, for instance, a previous surgery or intervention. In this case, a robotic means would be preferred, such as robotic arm, to ensure the relative position of the endoscope and the body. Once the relative position is known between the endoscope and the body, it would be feasible for the navigation system to navigate the endoscope accurately to the marked location in the body.

Processing means 640 can also be extended to simultaneously synchronize the endoscope images with CT or MR images for interventional imaging procedures. Such a synchronization could be established by computer software. Furthermore, processing means includes software modules to manipulate and/or process the acquired data on the computer display with one or more displays. Examples of possible data manipulation and/or processing includes software modules for magnification, staining or electronic filtering. Another example would be the manipulation and/or processing of the data to provide visualization of tissue of interest through blood.

As mentioned above, the endoscope include a user-hand control panel 650 to control the endoscope (See also FIG. 5). The endoscope of the present invention could also include control through voice commands 660 to control and select the type of electromagnetic source, type of filter, type of lens or type of image detector in each of their respective modules, as well as shaft positioning and mobility and distal end of shaft positioning and mobility. Such voice commands 660 would be the preferred mode of operation for a surgeon since it allows more precise operation and stability of the endoscope as well as it allows the surgeon to use his/her hands for other operations or interventions.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. A non-tethered macro-to-micro endoscope, comprising:
   (a) an electromagnetic source to deliver electromagnetic energy to a tissue inside a body;
   (b) an image detector to detect reflected electromagnetic energy from said tissue as real-time images;
   (c) a macro-to-micro lens set to change the magnification of said reflected electromagnetic energy at said image detector, wherein said lens set having different magnification levels of 1× for macroscopy and at least one for microscopy that is selected from a range of 5× to 200×;
   (d) a filter set to filter said reflected electromagnetic energy at said image detector, wherein said filter set comprises at least two types of filters;
   (e) a control means to control said macro-to-micro lens set by selecting one of said magnifications levels, said selected lens providing said magnification of said reflected electromagnetic energy; and
   (f) a control means to control said filter set by selecting one of said filters, said selected filter providing said filtering of said reflected electromagnetic energy.

2. The endoscope as set forth in claim 1, wherein said electromagnetic source is a light source or a modulated energy source in an electromagnetic spectrum.

3. The endoscope as set forth in claim 1, further comprising a control means to control said electromagnetic source.

4. The endoscope as set forth in claim 1, wherein said image detector comprises one or more CCD cameras, one or more ultrasound transducers, one or more infrared transducers, or one or more microwave transducers.

5. The endoscope as set forth in claim 1, wherein said filter set comprises a filter for changing luminescence.

6. The endoscope as set forth in claim 1, wherein said filter set comprises a filter for changing chrominance.

7. The endoscope as set forth in claim 1, further comprising a spread and spot means to spread and spot said electromagnetic energy at said tissue.

8. The endoscope as set forth in claim 1, further comprising a processing means for processing said detected images.

9. The endoscope as set forth in claim 8, wherein said processing means further comprises means for magnification, staining or electronic filtering.

10. The endoscope as set forth in claim 8, wherein said processing means processes said detected images in real-time.

11. The endoscope as set forth in claim 8, wherein said processing means further comprises means for image localization.

12. The endoscope as set forth in claim 8, wherein said processing means further comprises means for computerized image navigation to navigate said endoscope to a marked location in said detected image.

13. The endoscope as set forth in claim 1, further comprising a user-hand control panel to control said endoscope.

14. The endoscope as set forth in claim 1, further comprising a voice command control system to control said endoscope.

15. The endoscope as set forth in claim 1, further comprising a plurality of channels extending through said endoscope.

16. The endoscope as set forth in claim 14, further comprises control means to control said flexible shaft.

17. The endoscope as set forth in claim 1, further comprising a shaft, wherein said shaft is a flexible shaft.

18. The endoscope as set forth in claim 1, further comprising means for displaying said images.

19. The endoscope as set forth in claim 1, further comprising a wireless communications between said endoscope and processing means.

20. The endoscope as set forth in claim 1, wherein said endoscope operates with or without a translucent medium.

21. The endoscope as set forth in claim 1, wherein said endoscope is a catheter-based endoscope, a percutaneous endoscope, a transvascular endoscope or a trans-lymphatic endoscope.

22. A method of performing non-tethered macro-to-micro endoscopy, comprising the step of:
 (a) providing an electromagnetic source to deliver electromagnetic energy to a tissue inside a body;
 (b) providing an image detector to detect reflected electromagnetic energy from said tissue as real-time images;
 (c) selecting a magnification from a macro-to-micro lens set, wherein said magnification is 1× for macroscopy and at least one for microscopy that is selected from a range of 5× to 200×;
 (d) selecting a filter from a filter set, wherein said filter set comprises two or more filters;
 (e) controlling said macro-to-micro lens set by selecting one of said magnifications levels, said selected lens providing said magnification of said reflected electromagnetic energy; and
 (f) controlling said filter set by selecting one of said filters, said selected filter providing said filtering of said reflected electromagnetic energy.

23. The method as set forth in claim 22, wherein said endoscopy is performed with or without a translucent medium.

24. The method as set forth in claim 22, wherein said endoscopy is a catheter-based endoscopy, a percutaneous endoscopy, a transvascular endoscopy or a trans-lymphatic endoscopy.

25. A non-tethered macro-to-micro endoscope with a plurality of modules, comprising:
 (a) an electromagnetic source module to deliver electromagnetic energy to a tissue inside a body;
 (b) an image detector module to detect reflected electromagnetic energy from said tissue as real-time images;
 (c) a macro-to-micro lens set module to change the magnification of said reflected electromagnetic energy at said image detector, wherein said lens set having different magnification levels of 1× for macroscopy and at least one for microscopy that is selected from a range of 5× to 200×;
 (d) a filter set module to filter said reflected electromagnetic energy at said image detector, wherein said filter set comprises at least two types of filters;
 (e) a control means to control said electromagnetic source module;
 (f) a control means to control said macro-to-micro lens set by selecting one of said magnifications levels, said selected lens providing said magnification of said reflected electromagnetic energy; and
 (g) a control means to control said filter set by selecting one of said filters, said selected filter providing said filtering of said reflected electromagnetic energy.

26. The endoscope as set forth in claim 25, wherein said electromagnetic source module is a light source or a modulated energy source in an electromagnetic spectrum.

27. The endoscope as set forth in claim 25, wherein said image detector module comprises one or more CCD cameras, one or more ultrasound transducers, one or more infrared transducers, or one or more microwave transducers.

28. The endoscope as set forth in claim 25, wherein said filter set module comprises a filter for changing luminescence.

29. The endoscope as set forth in claim 25, wherein said filter set module comprises a filter for changing chrominance.

30. The endoscope as set forth in claim 25, further comprising a spread and spot means module to spread and spot said electromagnetic energy at said tissue.

31. The endoscope as set forth in claim 25, further comprising a processing means for processing said detected images.

32. The endoscope as set forth in claim 31, wherein said processing means further comprises means for magnification, staining or electronic filtering.

33. The endoscope as set forth in claim 31, wherein said processing means processes said detected images in real-time.

34. The endoscope as set forth in claim 31, wherein said processing means further comprises means for image localization.

35. The endoscope as set forth in claim 31, wherein said processing means further comprises means for computerized image navigation to navigate said endoscope to a marked location in said detected image.

36. The endoscope as set forth in claim 25, further comprising a user-hand control panel to control said endoscope.

37. The endoscope as set forth in claim 25, further comprising a voice command control system to control said endoscope.

38. The endoscope as set forth in claim 25, further comprising a plurality of channels extending through said endoscope.

39. The endoscope as set forth in claim 25, further comprising a shaft, wherein said shaft is a flexible shaft.

40. The endoscope as set forth in claim 39, further comprises control means to control said flexible shaft.

41. The endoscope as set forth in claim 25, further comprising means for displaying said images.

42. The endoscope as set forth in claim 25, further comprising a wireless communications between said endoscope and processing means.

43. The endoscope as set forth in claim 25, wherein said endoscope operates with or without a translucent medium.

44. The endoscope as set forth in claim 25, wherein said endoscope is a catheter-based endoscope, a percutaneous endoscope a transvascular endoscope or a trans-lymphatic endoscope.

45. A method of performing non-tethered macro-to-micro endoscopy with a plurality of modules, comprising the step of:
   (a) providing an electromagnetic source module to deliver electromagnetic energy to a tissue inside a body;
   (b) providing an image detector module to detect reflected electromagnetic energy from said tissue as real-time images;
   (c) providing a macro-to-micro lens set module to change the magnification of said reflected electromagnetic energy at said image detector, wherein said lens set having different magnification levels of 1× for macroscopy and at least one for microscopy that is selected from a range of 5× to 200×;
   (d) providing a filter set module to filter said reflected electromagnetic energy at said image detector, wherein said filter set comprises at least two types of filters;
   (e) a control means to control said electromagnetic source module;
   (f) a control means to control said macro-to-micro lens set by selecting one of said magnifications levels, said selected lens providing said magnification of said reflected electromagnetic energy; and
   (g) a control means to control said filter set by selecting one of said filters, said selected filter providing said filtering of said reflected electromagnetic energy.

46. The method as set forth in claim 45, wherein said endoscopy is performed with or without a translucent medium.

47. The method as set forth in claim 45, wherein said endoscopy is a catheter-based endoscopy, a percutaneous endoscopy, a transvascular endoscopy or a trans-lymphatic endoscopy.

48. The method as set forth in claim 45, further comprising a shaft, wherein said shaft is a flexible shaft.

* * * * *